United States Patent [19]
McGinnis

[11] Patent Number: 4,823,828
[45] Date of Patent: Apr. 25, 1989

[54] PRESSURE RELIEF VALVE

[76] Inventor: Gerald E. McGinnis, 131 Kelvington Dr., Monroeville, Pa. 15146

[21] Appl. No.: 55,077

[22] Filed: May 28, 1987

[51] Int. Cl.$^4$ .............................................. A62B 9/02
[52] U.S. Cl. ............................... 137/102; 128/205.24; 137/469; 251/337; 267/180
[58] Field of Search ............... 137/102, 469, 540, 494, 137/484.2; 267/166, 180; 251/337; 128/203.11, 205.24, 204.26

[56] References Cited

U.S. PATENT DOCUMENTS

| | | | |
|---|---|---|---|
| 2,820,469 | 1/1958 | Seeler | 137/64 |
| 2,863,446 | 12/1958 | Huxley, III et al. | 128/29 |
| 2,947,314 | 8/1960 | Bloom | 137/64 |
| 2,954,793 | 10/1960 | Seeler | 137/64 |
| 3,088,477 | 5/1963 | Bloom | 137/64 |
| 3,276,462 | 10/1966 | Matchett | 137/64 |
| 3,630,197 | 12/1971 | Hirano | 128/188 |
| 3,751,025 | 8/1973 | Beery et al. | 267/180 X |
| 3,799,185 | 3/1974 | Milnes et al. | 137/102 |
| 3,819,169 | 6/1974 | Imme et al. | 267/180 X |
| 3,872,875 | 3/1975 | Raidl | 137/469 X |
| 4,111,407 | 9/1978 | Stager | 267/166 X |
| 4,207,884 | 6/1980 | Isaacson | 128/200 |
| 4,350,176 | 9/1982 | Lace | 137/469 X |
| 4,406,302 | 9/1983 | Olesen | 137/469 X |
| 4,411,285 | 10/1983 | Oswell | 137/112 |
| 4,446,859 | 5/1984 | Pederson | 128/204 |
| 4,574,797 | 3/1986 | Christianson | 128/204 |
| 4,592,384 | 6/1986 | Cappa et al. | 137/494 |
| 4,616,646 | 10/1986 | Beaussant | 137/102 X |
| 4,622,964 | 11/1986 | Flynn | 137/102 X |

OTHER PUBLICATIONS

*Engineering Fluid Mechanics*, pp. 188-195, Roberson and Crowe, Houghton Mifflin Co, 1980.

*Primary Examiner*—Stephen Hepperle
*Attorney, Agent, or Firm*—Carothers & Carothers

[57] ABSTRACT

An inhalation/exhalation valve for use in conjunction with a medical respiration apparatus to maintain an adjustable positive end expiration pressure through incorporation of novel valving elements including a novel, adjustable spring for establishing and maintaining the threshhold pressure of exhalation and a novel flow control valve disk structure which utilizes the dynamic pressure of exhalation flow to assist in providing control over and fine adjustability of the valve disk motion and which further permits continuous supply flow during both the inhalation and exhalation portions of the patient's breathing cycle.

8 Claims, 2 Drawing Sheets

PRESSURE RELIEF VALVE

BACKGROUND OF THE INVENTION

In the art of respiration therapy and apparatus, it is well known to employ respiration systems to provide positive and expiration pressure as a therapy for intensive patient care. The effect of such therapy on the pulmonary system is dramatic and beneficial for a variety of disease entities. A valve which can be used in such respiration systems to control positive and expiratory pressure in commonly referred to as a PEEP valve.

In the medical literature, the PEEP valve is defined as a valve which exhibits threshold resistance. That is to say, a threshold resistor should allow no exhalation flow until exhalation pressure equals a predetermined threshold pressure. Above the threshold pressure, the valve should allow exhalation flow rates of up to 200 to 300 liters per minute without any significant increase in pressure drop across the valve. By significant increases is meant an increment exceeding approximately 10% of the threshold resistance value, for example.

Many valve structures known in the prior art are intended to provide control of inhalation and exhalation flow in respiration systems. In particular, the art includes many examples of PEEP valves whose intended function is to provide the desired exhalation threshold resistance as above described. For example, U.S. Pat. No. 2,954,793 discloses an inhalation/exhalation valve which includes a flexible disk inhalation valve element which is carried on an exhalation valve member to accommodate one way inhalation flow therethrough. The patent also discloses an hourglass shaped spring which biases the exhalation valve closed.

Other documents disclosing spring biased exhalation valve elements, and specifically conical springs for biasing the valve element, include U.S. Pats. Nos. 4,411,285; 2,863,446; 3,088,477; 3,630,197 and 3,276,462.

Among other patent art known to me, U.S. Pat. No. 4,574,797 discloses a second stage regulator for an underwater breathing apparatus which includes a flexible flap-type valve member. U.S. Pat. No. 2,820,469 discloses another combined inhalation/exhalation valve. U.S. Pat. No. 3,799,185 discloses yet another such valve, as does U.S. Pat. No. 4,207,884. Both of these patents appear to disclose a flange or skirt formed on the perimeter of a valve disk element. Other patents pertaining generally to breathing gas flow control include numbers U.S. Pat. Nos. 4,446,859; 2,947,314 and 4,592,384.

In the prior art the desirable performance criteria of a threshold resistor have required that very soft springs be used to preload a valve disk which covers a port that is exposed to the controlled pressure. Such devices generally require a very soft and long-loading spring which has a high ratio of preload deformation to displacement of the valve disk during exhalation flow through the valve. In this manner, the designer is better able to predict the force increment required to allow the disk to open a sufficient distance for the desired exhalation flow rates to occur. However, when one uses such a long, soft spring in a PEEP valve, or even the conventional conical springs, adjustability of the valve threshold pressure over a range useful for clinical application (i.e., approximately 3 to 25 cm H₂O) becomes difficult because the preload deformation of the spring has to be relatively large to achieve the desired range of pressure variation. A shorter conventional spring will tend to be too stiff for use in the range of low operation pressures specified. Preferably, the spring should be very soft at initial valve opening and throughout the desired pressure range, while becoming progressively stiffer in a non-linear manner with incremental opening of the exhalation valve. This can provide for a readily adjustable threshold resistance, and will also permit the valve to reliably maintain the selected threshold resistance throughout the exhalation cycle and for a relatively wide range of exhalation flow rates.

As has been mentioned, it is important that a PEEP valve not only be readily adjustable with a high degree of precision, additionally it should exhibit the performance criterion of pressure or threshold resistance stability. That is, whatever the threshold resistance setting to which the valve has been adjusted, that threshold resistance should be maintained throughout the normal range of exhalation flow rates in order to ensure that a constant, positive end expiratory pressure value will be maintained regardless of the patient's expiratory flow rate.

Although the prior art is replete with valves which are intended to function effectively as PEEP valves, practitioners in the art continue to seek improvements in valve adjustability and operating stability.

BRIEF SUMMARY OF THE INVENTION

The present invention contemplates a novel adjustable PEEP valve wherein a conical spring is utilized to impart the bias needed to establish threshold resistance in the valve. The spring has non-uniform coil density which varies over the length of the spring. An adjustment mechanism such as an adjustment screw cooperates with the spring to provide for selective adjustment of the valve threshold resistance.

The invention also contemplates a moveable exhalation valve element which is biased toward its closed position by the above characterized spring, and which includes an exhalation flow reversing structure which cooperates with the exhalation flow path defined within the valve to impart a reversal of flow direction to the exhalation flow as it passes from the valve exhaust ports. The valve is so structured that this reversal of exhalation flow direction provides for utilization of the hynamic pressure of exhalation effort by the patient to help control operation of the valve and thereby, in cooperation with the novel spring structure, further enhance adjustability and operating stability of the valve.

Other novel aspects of the valve include a provision therein for maintaining breathing gas flow continuously during both inhalation and exhalation portions of the breathing cycle by directing breathing gas flow to the exhalation valve exhaust ports only during the exhalation portion of the breathing cycle. This can result in increased stability of a breathing gas flow supply pressure by reducing the incidence of pressure transients within the gas supply tubing network.

It is therefore one general object of the invention to provide a novel and improved adjustable PEEP valve for use in respiratory therapy.

A more specific object of the invention is to provide a novel PEEP valve with structural improvements for enhanced adjustability and operational stability.

A more specific object of the invention is to provide a PEEP valve with a movable valving element having an exhalation flow reversing structural means, the valve element being biased toward the closed position by a conical coil spring which has a coil density that varies over the length of the spring in a predetermined manner; the spring and the flow reversing structure being effective to provide improved valve operation reliability, adjustability and stability.

These and other objects and further advantages of the invention will be more clearly understood upon consideration of the following detailed description and the accompanying drawings, in which.

Figure 1:
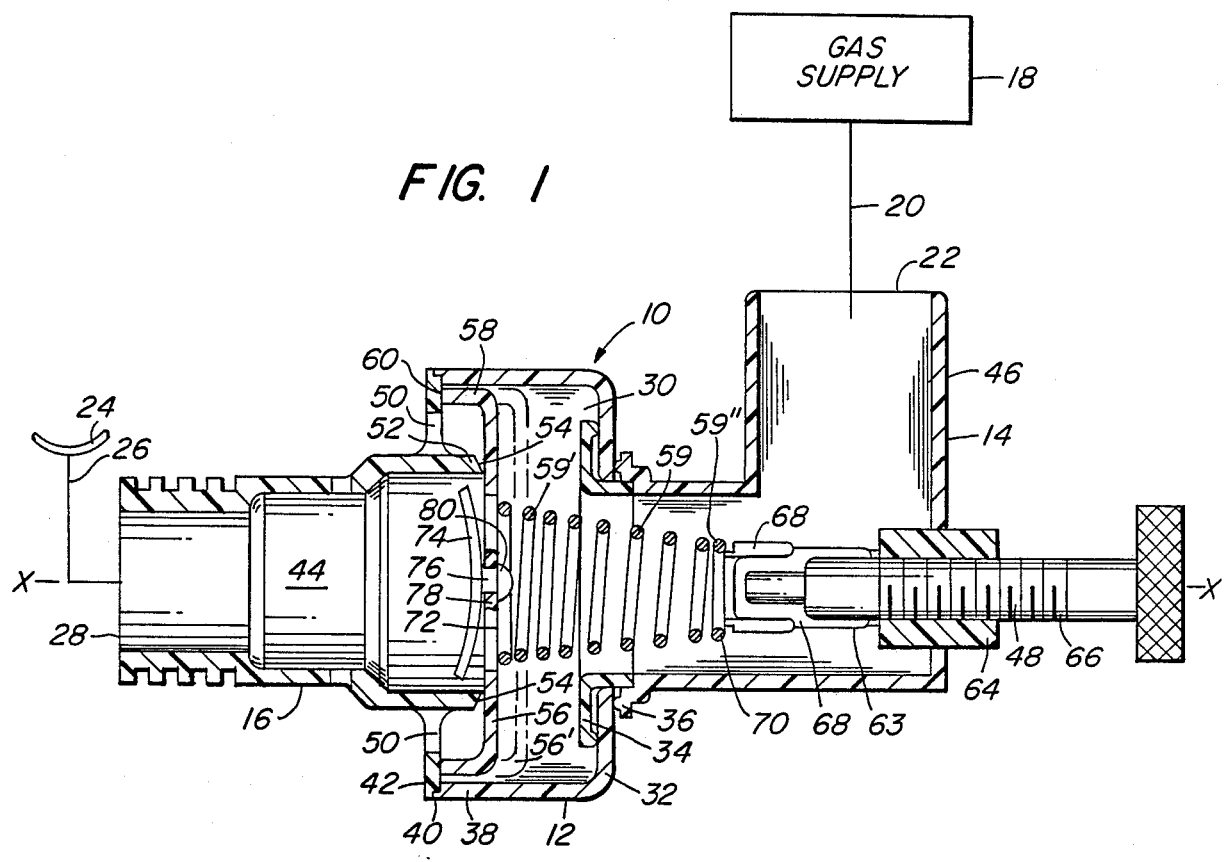
FIG. 1 is a sectioned side elevation of a valve according to one presently preferred embodiment of the invention.

There is generally indicated at 10 in FIG. 1 a valve comprised of an assembly of body parts including a main valve body 12 fixed coaxially adjacent a breathing gas inlet body portion 14 and a patient supply body portion 16. As is well known, a suitable medical gas supply source 18 is provided to supply medical gas via a delivery conduit 20 to an inlet end 22 of body portion 14. Similarly, a mask 24 or other suitable appliance is connected by means of a conduit 26 to an outlet end 28 of body portion 16 for delivery of the supply gas to a patient (not shown) and to carry exhalation flow from the patient to exhaust ports 50. The valve 10 thus is interposed between supply source 18 and mask 24 to permit inhalation flow and to provide for exhalation flow at a controlled positive expiratory pressure to achieve the beneifts of PEEP therapy for the patient. Inasmuch as the elements above described, insofar as they pertain to PEEP therapy, are well known to those versed in the art and form no part of the instant invention, further detailed description thereof is believed unnecessary for an understanding of the invention.

The body portion 12 is comprised of a generally stepped cylindrical, open ended member of rigid molded plastic construction, for example, which defines a through opening 30. An inhalation end portion 32 of body member 12 accommodates a generally annular mounting flange 34 which cooperates with a mounting flange portion 36 of body member 14 to secure body member 14 coaxially with respect to inhalation end portion 32. Similarly, an exhalation end portion 38 of the body member 12 includes a stepped annulus 40 which cooperates with a mounting flange portion 42 of body member 16 to secure the same coaxially with respect to body member 12. As body members 14 and 16, like body member 12, may be of rigid molded plastic, the assembly thereof into a unified structure as above described may be achieved by such means as a suitable bonding system, a solvent weld bonding agent for example.

The assembly of body elements as above described defines a generally stepped-cylindrical structure having a combined inhalation/exhalation gas flow path 44 extending generally coaxially therein. It will be noted, however, that body member 14 includes a right angle portion 46 which projects laterally of the longitudinal axis X—X of valve 10 and having the open end portion 22. The portion 46 may typically have a manual breathing bag mounted thereon.

Figure 4:
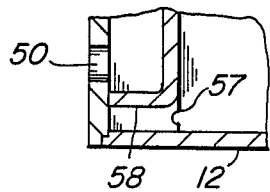
FIG. 4 is an enlarged fragmentary portion of a sectional view similar to FIG. 1 showing an alternative structure.

Within flange portion 42 there is formed an outlet means as a plurality of exhalation ports 50 which accommodate expiratory flow that passes via mask 24 and conduit 26 into exhalation end 28 of valve 10 thence to the atmosphere, or to a suitable collection facility (not shown) via the ports 50. A valve seat portion 52 of body member 16 extends coaxially into the space 30 defined within body member 12 to provide a valve seat 54 upon which an exhalation valve disc 56 seats under the bias of a spring 59. It will be noted that expiratory flow passes via conduit 26 and within passage 44 over seat 54, whereat its flow direction is reversed as it proceeds to exhalation ports 50. Thus, reversal of expiratory flow direction occurs immediately adjacent to valve disc 56 during patient exhalation. This reversal of flow direction is utilized to impart an increment of operating control to the exhalation valve. To provide the described flow reversal, valve disc 56 is provided with a flow directing means in the form of a depending peripheral skirt portion 58 which projects from valve disc 56 toward ports 50 radially outward thereof. When valve disc 56 is seated upon seat 54, the outermost annular seat 60 of skirt portion 58 may be seated upon flange portion 42 radially outward of ports 50 to seal ports 50 from the peripheral space surrounding skirt 58. Alternatively, a bellows or diaphragm 57 may be employed in lieu of or in addition to annular seat 60 to close the peripheral space radially outward of skirt 58 as shown in FIG. 4.

Referring again to FIG. 1, disc 56 remains thus seated so long as the seating bias of spring 59 is not overcome by patient expiratory effort. Spring 59 comprises an elongated coil spring of generally conical form having its larger diameter turns (e.g. 59′) at the end thereof adjacent to valve disk 56 and its smaller diameter turns (e.g. 59″) adjacent the opposite end thereof and engaged by a spring engaging assembly 62 of adjustment screw assembly 48. Additionally, as shown spring 59 exhibits a variation of coil density over its length with the greater coil density (coils per inch) being at the large diameter end thereof, and the lesser coil density being at the smaller diameter end thereof.

Spring 59 is supported by engagement thereof between disk 56 and adjustment screw assembly 48, specifically in that assembly 48 includes a threaded insert 64 through which there is passed an elongated threaded adjustment screw 66 which engages adjacent its innermost end the described spring engaging assembly. The assembly 62 in turn comprises a collar member 68 which engages the smaller diameter end 70 of spring 59 and is freely rotatable with respect to a cap member 63 such that adjustment of screw 66 by rotation thereof serves to incrementally compress, or permit longitudinal expansion of, the spring 59 without application of torque thereto.

Valve disk 56 also includes a plurality of inhalation ports 72 disposed within the diameter of disk 56 engaged by seat 54, and a flexible flap valve element 74 affixed centrally of disk 56 to provide one-way flow for inhalation only through ports 72 while precluding reverse flow of exhalation gases therethrough. Flap valve element 74 thus is affixed to the downstream side (with respect to inhalation flow) of disk 56 as by a stud portion 76 thereof which passes through a central opening 78 formed in disk 56 and terminating in an enlarged head portion 80 which secures flap valve 74 with respect to disk 56 as described.

As can be seen from the above description, the valve 10 operates to provide for inhalation flow from gas supply source 18 via conduits 20 and 26 and mask 24 to the patient upon demand by allowing gas flow through inhalation ports 72 and past flap valve 74 with disk 56 seated upon seat 54. Since in this configuration the sealing or seating edge 60 of peripheral skirt 58 also is seated on flange 42, exhalation ports 50 are completely isolated from gas supply flow. Alternatively, diaphragm 57 may be employed in lieu of seat 60 to provide the same function, and additionally to preclude supply flow to exhaust ports 50 when valve disk 56 is lifted (i.e. during exhalation).

During the exhalation phase of a patient's breathing cycle, patient effort creates elevated pressure within conduit 26 and body member 16. The exhalation pressure very quickly exceeds gas supply pressure thus closing flap valve 74 to preclude backflow of exhalation gases toward the gas supply. When the pressure of exhalation effort reaches the established threshold resistance level and overcomes the bias of spring 59, disk 56 is lifted to the position indicated at 56', at which position patient expiration effort and spring bias are equalized.

In the lifted or open position as shown as 56', disk 56 is clear of seat 54 and additionally seat 60 is separated from flange 42. Thus, exhalation flow proceeds around seat 54 and to exhalation ports 50, reversing its flow direction as it goes. Additionally, if diaphragm 57 is not used, gas flowing from supply 18 via conduit 20 and body member 14 has a flow path within space 30 around the exterior periphery of skirt portion 58 and to exhalation ports 50. Without diaphragm 57, exhalation flow is precluded from by-passing exhalation ports 50 and proceeding through the gap between flange 42 and skirt seating surface 60 by means of the supply flow, and the continuing flow of supply gas during exhalation provides improved control over supply side gas pressure.

The spring 59 with its varying diameter and density of coils operates to provide improved adjustability for threshold resistance settings of valve 10, as has been noted. In general, a very soft, large diameter coil spring with a relatively high coil density would be the spring of choice for low level threshold resistance pressures because the magnitude of valve disk movement or displacement from its seat must be relatively large at low threshold resistance pressures to permit the requisite exhalation flow rates. On the other hand, at higher threshold resistance pressures, valve disk movement or displacement is relatively smaller for the same exhalation flow rates, thus calling for application of stiffer spring bias earlier in the displacement of the valve disk.

According to the present invention the disclosed spring, when adjusted for low-level threshold resistance pressure, operates by exposing a relatively larger number of larger diameter coils to the valve disk, and this provides the requisite soft spring resistance for the relatively larger valve disk displacement that is required. As the spring load is adjusted by manipulation of screw 66 to establish higher threshold resistance pressures, the spring 59 tends to close or collapse on itself, with the larger coils bottoming out and becoming inoperative. The smaller coils, which are relatively stiffer, thus provide the biasing action on the valve disk at higher threshold resistance levels. It has been found that the useful range of threshold resistance pressures (e.g. 3 to 25 cm $H_2O$) may be achieved by utilizing a spring with a ratio of maximum spring coil diameter to a minimum spring coil diameter of approximately 2 to 1 to 2.5 to 1, although it will be understood that higher ratios may be used if higher ranges of threshold resistance are desired. It has also been found that in such a spring the coil density should vary by a ratio of approximately 2 to 1 from one end of the spring to the other. Such a spring, with the spring wire diameter selected to provide the requisite initial softness of response, provides the desired performance as regards operational stability and adjustability of threshold resistance.

The above described technique and structure for reversing exhalation flow direction as it passes seat 54, and the use of disk 56 and skirt portion 58 as reaction surfaces to reverse such flow direction, allows the valve to utilize the dynamic pressure head of exhalation to help achieve low pressure drop after threshold resistance pressure has been reached. As valve disk 56 lifts in response to patient exhalation effort, the dynamic pressure required to reverse exhalation flow direction becomes useful in moving or displacing valve disk 56 to allow higher through flow. More specifically, the pressure drop across the PEEP valve should be essentially constant over a wide range of throughflow rataes. Such performance implies a wide range of movement of the valve disc 56 to accomodate the varying flowrates, which causes the spring to experience a wide range of deflection. In other words, the air pressure must increase some amount to cause the disc to move far enough to accomodate the gas flow.

In this system, the important pressure is the static pressure component of the total pneumatic pressure. On the other hand, the pressure which causes disc movement is comprised of both static and dynamic components.

This invention provides enhanced valve performance because high volumetric exhalation flow translates into high massflow rates as well. By reversing the flow direction, as disclosed, the dynamic pressure component becomes significant at high flowrates and assists the static component in moving the disc against the spring force. In this manner, the static pressure changes are smaller, i.e. the valve performance is better, than would result if the gas were allowed to vent radially rather than being reversed or turned through the 180 degree turn as disclosed.

This aspect of the invention would be beneficial in any PEEP valve design but is more so when used in combination with the above-described adjustable spring. In the disclosed valve, excellent performance has been achieved over a wide range of respiratory pressures.

Figure 2:
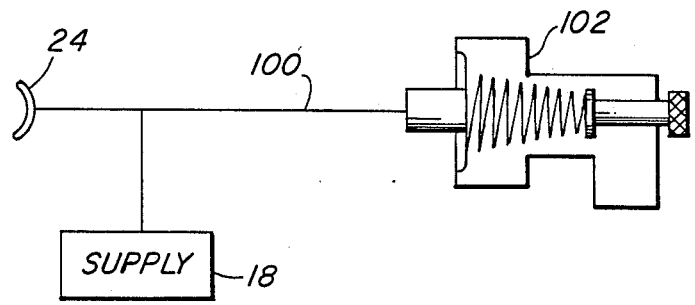
FIG. 2 is a schematic illustration of an alternative valve structure.

The novel structural features disclosed hereinabove may of course be employed in other valve configurations than the valve of FIG. 1. For example, there is shown in FIG. 2 a more conventional PEEP arrangement wherein gas supply 18 supplies breathing as via suitable flow conduits to mask 24 for breathing thereof by a patient (not shown). Supply pressure head control and exhalation exhaust both are provided by a valve 102 which is connected to supply 18 and mask 24 in a well known configuration as by a suitable conduit 100. Valve 102 includes an adjustable conical spring which preloads a valve disk having a depending skirt. Either the spring alone, the depending skirt alone, or both operating together enhance valve operation as has been above described with reference to FIG. 1.

Figure 3:
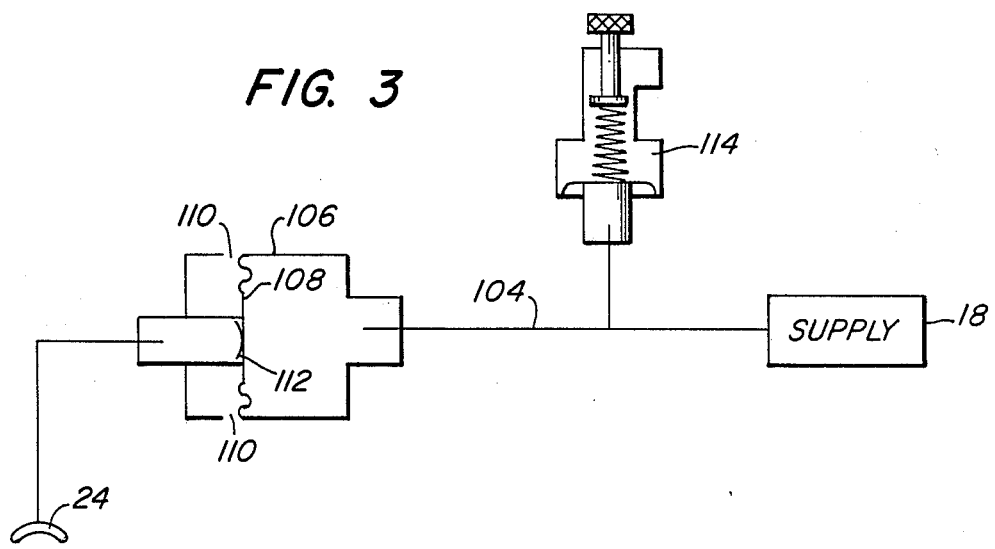
FIG. 3 is a schematic illulstration of a further alternative structure.

In another alternative arrangement, FIG. 3 shows a breathing gas system wherein supply 18 communicates with mask 24 via a conduit 104 having an inline exhaust valve 106 in which an exhaust valve element 108 is movable in response to the pressure differential on opposite sides thereof to open and close exhaust ports 110. A flexible flap check valve element 112 is carried by valve element 108 in much the same manner as flap valve 74 is carried by the valve disk 56 as above described, to permit gas supply flow from supply 18 to mask 24 when valve element 108 is closed. Another valve 114 is connected to conduit 104. Valve 114 includes an adjustable conical spring and valve disk with depending skirt which operates in the manner above described with reference to FIG. 1 to control supply pressure or, more generally, the pressure heading conduit 104. Valve 114 thus also controls the pressure on the supply side of valve 106. This is what controls threshold resistance for valve 106 as pressure behind valve element 108 must be overcome by the patient's exhalation effort before exhalation flow may begin.

In all of the described embodiments, the conical spring and valving element with depending skirt operate to provide enhanced control over threshold exhalation resistance in PEEP type breathing apparatus. Of course, it will be understood that for any embodiment of this invention the outlet ports 50 may be located in alternative locations other than that shown in FIG. 1. That is, the flow reversing effect, and the dynamic pressure benefit thereof as above described, results from the valve disc and seat configuration rather than from the location of the outlet ports 50.

According to the description hereinabove there is provided by the instant invention a novel and improved inhalation/exhalation valve structure for use in respiratory PEEP therapy. The novel valve offers, among other benefits, enhanced consistency of performance, reliability, and ease of adjustment over prior PEEP valves.

Of course, I have contemplated various alternative and modified embodiments of the invention, and such also would certainly occur to others versed in the art, once apprised of my invention. Accordingly, it is intended that the invention be construed as broadly as permitted by the scope of the claims appended hereto.

I claim:

1. In a valve for controlling medical gas delivery to a patient and for providing a threshold resistance for positive end expiratory pressure therapy for such
    pressure valve for administering positive end expiratory pressure therapy to a patient by providing a threshold resistor which includes a valve element that is biased toward a closed position by a variable bias to provide threshold resistance which prevents exhalation flow from such a patient until such threshold resistance is overcome, the improvement comprising:
    a spring bias means for biasing the valve element toward the closed position with said spring bias means comprising a conically formed coil spring having varying coil density with the maximum coil density adjacent the larger diameter end thereof and a minimum coil density adjacent the smaller diameter end thereof.

2. The combination as claimed in claim 1 wherein said valve body includes an inhalation opening and said gas flow passage communicates between said inhalation and exhalation openings, and the said exhalation outlet means being in communication with said gas flow passage intermediate said inhalation and exhalation openings.

3. The combination as claimed in claim 2 additionally including one-way flow check valve means carried by said valve element to permit inhalation flow to pass through said valve from said inhalation opening to said exhalation opening when said valve element is seated on said seat means.

4. The combination as claimed in claim 3 wherein said seat means isolates said outlet means from said gas flow passage when said valve element is seated thereon.

5. The combination as claimed in claim 4 additionally including adjustment means for selective adjustment of the bias of said spring bias means.

6. In a positive end expiratory pressure valve for administering positive end expiratory pressure therapy to a patient by providing a threshold resistor which includes a valve element that is biased toward a closed position by a variable bias to provide threshold resistance which prevents exhalation flow from such a patient until such threshold resistance is overcome, the improvement comprising:
    a spring bias means for biasing the valve element toward the closed position with said spring bias means comprising a conically formed coil spring having varying coil density with the maximum coil density adjacent the larger diameter end thereof and a minimum coil density adjacent the smaller diameter end thereof.

7. The improvement as claimed in claim 6 wherein said spring bias means includes said maximum minimum coil densities adjacent the respective larger and smaller diameter ends thereof when in a free or uncompressed state.

8. The improvement as claimed in claim 7 additionally including adjustment means for adjusting the bias of said spring bias means.

* * * * *